United States Patent [19]

Kondo et al.

[11] Patent Number: 5,168,047
[45] Date of Patent: Dec. 1, 1992

[54] METHOD FOR IMPROVEMENT OF SENSITIVITY OF ENZYME DETECTION BY PHOTO IRRADIATION

[75] Inventors: Koichi Kondo, Sohraku; Marvin A. Motsenbocker, Amagasaki, both of Japan

[73] Assignee: Takeda Chemical Industries, Inc., Osaka, Japan

[21] Appl. No.: 619,117

[22] Filed: Nov. 28, 1990

[30] Foreign Application Priority Data

Dec. 4, 1989 [JP] Japan .................................. 1-315028

[51] Int. Cl.$^5$ ......................... C12Q 1/28; G01N 21/62
[52] U.S. Cl. ........................................... 435/28; 435/8; 435/962; 435/968; 436/172; 436/805
[58] Field of Search ..................... 435/28, 8, 968, 962; 436/172, 805

[56] References Cited

U.S. PATENT DOCUMENTS

| | | | |
|---|---|---|---|
| 4,835,101 | 5/1989 | Kao et al. | 435/28 |
| 4,842,997 | 6/1989 | Carter et al. | 435/28 |
| 4,859,583 | 8/1989 | Heller et al. | 435/28 |

FOREIGN PATENT DOCUMENTS 0087959 7/1983 European Pat. Off. .
0193895 10/1986 European Pat. Off. .
2095830 11/1978 United Kingdom .

OTHER PUBLICATIONS

Scott, G, "Atmospheric Oxidation and Antioxidants" Elsevier Pub. Co.: Amsterdam 1965, p. 93.
"Encyclopedia of Polymer Science And Technology" vol. 14, Wiley (1971), pp. 125-129.
Thorpe et al, *Biochemical and Biophysical Research Communications*, vol. 119, No. 2, pp. 481-487, 1984.

*Primary Examiner*—Johnnie R. Brown
*Assistant Examiner*—Abdel A. Mohamed
*Attorney, Agent, or Firm*—David G. Conlin; Donald R. Castle

[57] ABSTRACT

A method for improvement of a sensitivity of enzyme detection by irradiating enzymatic reaction components containing free radical contaminants with light ranging from the ultraviolet through the visible light spectrum prior to an enzyme detection reaction is disclosed.

8 Claims, 5 Drawing Sheets

METHOD FOR IMPROVEMENT OF SENSITIVITY OF ENZYME DETECTION BY PHOTO IRRADIATION

FIELD OF THE INVENTION

The present invention relates to methods for improvement of enzyme detection sensitivity and particularly, to light irradiation methods for improvement of detection sensitivity. The method of the present invention can be used for detecting enzymes and in the field of diagnostic assays utilizing enzyme detection.

BACKGROUND OF THE INVENTION

Diagnostic assays using antibodies and those using nucleic acids have been found to be useful for detection or determination of very low concentrations of various medically, environmentally or industrially important organic substances (e.g., antigens, antibodies, DNA, RNA, etc.) in liquid media. Nowadays, clinical tests or diagnostic test kits which have resulted from the embodiment of these methods are practically used because the tests can be rapidly and readily conducted by using them.

When using such a kit, usually, a body fluid containing an unknown amount of an organic substance to be tested is bound to a solid phase or other chemical substance (e.g., an enzyme-labeled antibody, etc.). In many cases, the solid phase used for the kit has an immobilized antigen (hapten), antibody or nucleic acid on its surface, and such a substance takes part in a competitive binding reaction or binding pair formation reaction with the above organic substance or other chemical substance. Usually, this binding reaction is conducted prior to a reaction for detection or determination, i.e., a reaction for generating a signal such as light, electric current or the like in a measurable amount which varies in proportion to the concentration of a substance to be tested (usually, mediated by an enzyme which correlates to concentration of a substance to be tested as described hereinafter).

In many cases, an enzymatic reaction is employed to generate a signal because amplification can thus be utilized. Usually, determination of the amount of an enzyme is conducted by maintaining the enzyme under specific incubation conditions (including pH, salt, temperature, substrate, composition of buffer solution, etc.) for a certain period of time, and then measuring the product of the enzymatic reaction.

In a most sensitive method, after separation or washing of an enzyme bound to a solid phase carrier, the enzyme is incubated in a specific medium to cause an enzymatic reaction to generate light as a signal (photo-signal). Under these conditions, sensitivities are often limited due to limitation of the catalytic reaction rate of the enzyme or the apparatus used to measure the enzymatic activity. The sensitivity of enzyme detection is of importance because it defines the sensitivity of detection of a substance to be tested [see Ekins et al., J. Biolum. Chemilum., 4, 59–78 (1989)]. Therefore, improvement in the sensitivity of detection of an enzyme label has been desired and various studies are directed to this topic.

Further, there are problems and limitations peculiar to respective types of the conventional measurements of enzymes. For example, an enzyme which catalyzes a redox reaction is sensitive to substances which chemically interfere with the reaction such as ascorbate, sulfhydryl compounds, iron and the like. In an enzymatic reaction, it is necessary to maintain the concentration of such interfering substances as low as possible, and various attempts to remove the interfering substances or to minimize their influence thereof have been made to improve this kind of technique. For example, Scott and Kricka [Bioluminescence and Chemiluminescence, 237–240 (1987)] disclose an improved method for purifying the substrate luminol which is subjected to an enzymatic reaction with horseradish peroxidase (hereinafter sometimes abbreviated as HRP) to generate a photo-signal. However, even in the case of recrystallized luminol, a trace amount of impurities remain. In addition, impurities may be formed during storage of an aqueous solution of luminol. These impurities lower the sensitivity of enzyme detection. Furthermore, there is a problem that interfering substances are still present in impurities from other reaction components such as an enhancer used for enhancing the reaction of an enzyme with luminol, an organic solvent used for dissolving an enhancer, a buffer salt, substances absorbed on the surface of a reaction vessel and the like. Particularly, an enzyme which releases free radicals by reaction with an enhancer or the like is liable to be influenced by the above interfering substances. Namely, substances which quench free radicals in a solution to be subjected to readout, for example, impurities such as protein, other sulfhydryl compounds, various amino acids, phenols and quinones, readily react with free radicals to interfere with the measurement. Therefore, such an enzyme is very likely to undergo interference from the above substances. Another disadvantageous result caused by interference from the above substances is time lag. This time lag corresponds to a period of time required for consuming free radicals produced by reaction of an enzyme with interfering substances and, a chain reaction may be firstly initiated by free radicals produced after all the interfering substances have been consumed by reaction with free radicals [Morrison and Boyd, "Organic Chemistry", page 50 (1973)].

OBJECTS OF THE INVENTION

The main object of the present invention is to enhance detection sensitivity for enzymes that utilize a free radical reaction mechanism.

This object as well as other objects and advantages of the present invention will be apparent to those skilled in the art from the following description with reference to the accompanying drawings.

BRIEF EXPLANATION

SUMMARY OF THE INVENTION

The present inventors have studied intensively to improve sensitivity of detection of enzymes utilizing a free radical reaction mechanism. As a result, it has been found that detection sensitivity can be improved by modification of a material to be treated with light prior to generation of a signal to detect the enzyme. More particularly, it has been found that the sensitivity can be improved by formation of free radicals with a light source and, optionally, a photosensitive substance such as a photosensitive coloring matter or the like and reaction thereof with interfering substances prior to initiation of an enzymatic reaction to consume the interfering substances.

According to the present invention, there is provided a method for improvement of sensitivity of enzyme detection which comprises irradiating enzymatic reaction components containing free radical contaminants with light ranging from the ultraviolet through the visible light spectrum prior to the enzyme detection reaction.

DETAILED DESCRIPTION OF THE INVENTION

In the present invention, enzyme detection is conducted by using enzymatic reaction components thus treated by irradiation with light prior to the enzyme detection reaction. In general, it is preferable to conduct the enzyme detection reaction by means of chemiluminescence.

The term "free radical contaminants" used herein means impurities which consume free radicals formed by the reaction of an objective enzyme, and includes any substance which inhibits or interferes with an enzyme or enzymatic reaction for detecting the enzyme by utilizing a free radical reaction mechanism as described above. Particularly, the method of the present invention can be advantageously used for preventing enzyme detection from influence of interfering substances which quench free radicals.

The term "enzymatic reaction components" used herein means not only a solution containing a substance to be subjected to the reaction catalyzed by an objective enzyme, i.e., a solution containing a substrate of the enzyme, but also substances which are used in the enzymatic reaction such as chemilumigenic components (e.g., luminol, etc.), hydrogen peroxide, enhancers, solvents and the like. The detection of enzyme using the enzymatic reaction components thus treated by irradiation with light can be conducted under conditions suitable for a particular enzyme used according to the conventional method. The enzyme may be included in the enzymatic reaction components to be irradiated with light prior to an enzyme detection reaction. Alternatively, the enzyme may be added after irradiation with light. In general, it is preferred to add the enzyme after irradiation.

In many enzyme measurements and detections by means of enzymatic catalytic reactions, free radical intermediates are utilized, and such measurements and detections can be improved by employing the method of the present invention.

Examples of free radical producing enzymes to which the method of the present invention is applicable include laccase, ascorbate oxidase, peroxidases, ceruloplasmin and the like. It has been reported that reactions catalyzed by these enzymes involve free radical intermediates [Malstorm et al., The Enzymes, Vol 12, Second, page 574 (1975)], and these reactions are advantageously applicable to the method of the present invention. Among these reactions, particularly, reactions of horseradish peroxidase with an enhancer and the like are widely used for very high sensitivity assays. Other systems involving reactions of free radical species formed by activated oxygen with chemilumigenic components such as luminol, acridinium ester and the like are also applicable to the method of the present invention. In this group, xanthine oxidase is also included.

In the method of the present invention, the sensitivity can be advantageously improved by irradiating enzymatic reaction components with light in the presence of any photosensitive substance which forms free radicals or active oxygen upon absorption of light. For example, substances which can produce active oxygen or free radicals by visible light, for example, thionine, phenosafranine, toluidine blue, flavin mononucleotide, methylene blue and resazurin [Fridovich and Handler, Biochim. Biophys. Acta, 35, 546–547 (1959)] can be used as the photosensitive substances. Other well known photosensitizers, xanthine compounds, particularly, fluorescein, eosin, erythrosine, rose bengal and the like can also be used as the photosensitive substances. It is preferable to use photosensitive coloring matters which efficiently form free radicals and other active oxygen species such an singlet oxygen upon absorption of light, but do not show excessive quenching properties. Free radicals and active oxygen thus formed react with free radical quenching contaminants which interfere with the measurement and detection of enzymes Particularly, methylene blue, xanthine derivatives, flavin derivatives and the like are preferred. Usually, optimal concentration of the photosensitive substance is within the range between concentration for bringing to a maximum formation of free radicals and that for bringing to a minimum quenching thereof because many of these coloring matters may act as free radical quenchers. For example, methylene blue is useful within the range of 2 ng/ml to 100 ng/ml and, preferably, it brings to a most preferred result within the range of 5 to 15 ng/ml.

The irradiation of the enzymatic reaction components with light according to the present invention is illustrated in detail below.

When the photosensitive substance is included in the enzymatic reaction components, usually, visible light is used. However, other kinds of light can also be used. In so far as a wavelength spectrum of light is overlapped with that of the photosensitive substance, various kinds of light can be used. In general, preferably, irradiation is conducted by using a light source which can generate light having a wavelength corresponding to that of the maximum absorbance of the photosensitive substance used. For example, methylene blue has a main absorption band at 660 nm and, when methylene blue is irradiated with light of this wavelength, singlet oxygen is efficiently formed. Although pH of the aqueous solution of the enzymatic reaction components is not specifically limited, the solution has of pH preferably from 5 to 13, more preferably, 6 to 10. Further, although the temperature of the aqueous solution to be irradiated is not specifically limited, in view of the enzyme and the apparatus to be used, 20° to 37° C. is preferred.

The irradiation time is determined by the amount of light energy and concentration of the substance to be used. Usually, an irradiation time of 1 to 120 seconds is preferred. Preferably, a stand-by time is employed between light irradiation and the initiation of a luminol enzymatic reaction depending upon irradiation conditions. The standby time is preferably provided at about 0 to 120 seconds after irradiation.

When the aqueous solution of enzymatic reaction components is irradiated with ultraviolet light, many substances form free radicals. Sometimes, compounds including those quenching the free radicals are degraded by irradiation with ultraviolet light. Therefore, in the case of irradiation with ultraviolet light, the method of the present invention is preferably conducted in the absence of the above photosensitive substance. Since ultraviolet light is very active as described above, it is preferable to conduct the method of the present invention by irradiating the solution with ultraviolet light having a relatively long wavelength or visible light (250 to 400 nm) for a minimum exposure time. When the consumption of free radical contaminants such as interfering substances which quench free radicals is conducted by irradiation with ultraviolet light, a stand-by time between the light exposure step and the subsequent use of the solution can be employed and this is also of importance in view of lowering a high background caused by ultraviolet light.

One example of preferred embodiments of the present invention is the reaction of luminol with p-phenylphenol in the presence of HRP enzyme and hydrogen peroxide. In this reaction, methylene blue is included in the incubation medium, which contains enzymatic reaction components, prior to enzyme detection. The mixture is irradiated with white light prior to addition of hydrogen peroxide and HRP. This allows the sensitivity to be considerably improved.

p-Phenylphenol is one example of an enhancer and any known enhancer can be used.

Another advantageous feature of the present invention is reduction of time required for detecting an enzyme in a low concentration. The time required for detection can be reduced by consuming interfering substances to substantially remove time lag of an enzymatic reaction caused thereby. The consumption results from formation of free radicals due to excitement by irradiation. Still another advantageous feature of the present invention is reduction of the scale of reaction required for measurement of an enzyme concentration. Namely, this can result from an increase in total signal generated by the light irradiation treatment. Still another advantageous feature of the present invention is to permit assay of enzyme at low concentration by using reaction components having lower purities. To purify all components of a reaction mixture in acceptable purities costs a great deal or is inconvenient. On the contrary, according to the present invention, interfering substances which quench free radicals can be removed by merely irradiating a mixture of various components.

Another advantageous feature of the present invention is to unidimensionally correlate the amount of chemiluminescence with a concentration of HRP, i.e., to make the relationship between them linear. When an enzyme label is used in a signal generation step of a certain assay, existence of a linear relationship between enzyme concentration and the signal response must be particularly desirable because an algorithm to be used for conversion of the reactivity of the enzyme into the concentration thereof is remarkably simplified by such a relationship. Regarding HRP, one of the major problems is substantial reduction of chemiluminescence in proportion to enzyme concentration at concentration of about 1,000 atto-mol/ml or less (Janse et al., Journal of Bioluminescence and Chemiluminescence, 1989). However, according to the present invention, chemiluminescent signals are preferentially intensified in successively lowering concentrations of an enzyme and the above linear relationship can be improved. A further advantageous feature of the present invention is to improve coefficient of variation (CV) in enzymatic signal measurement. Namely, according to the present invention, coefficient of variation upon counting can be improved by increasing the total amount of chemiluminescence. Such an improvement of counting efficiency is very useful in analytical assays.

Figure 5:
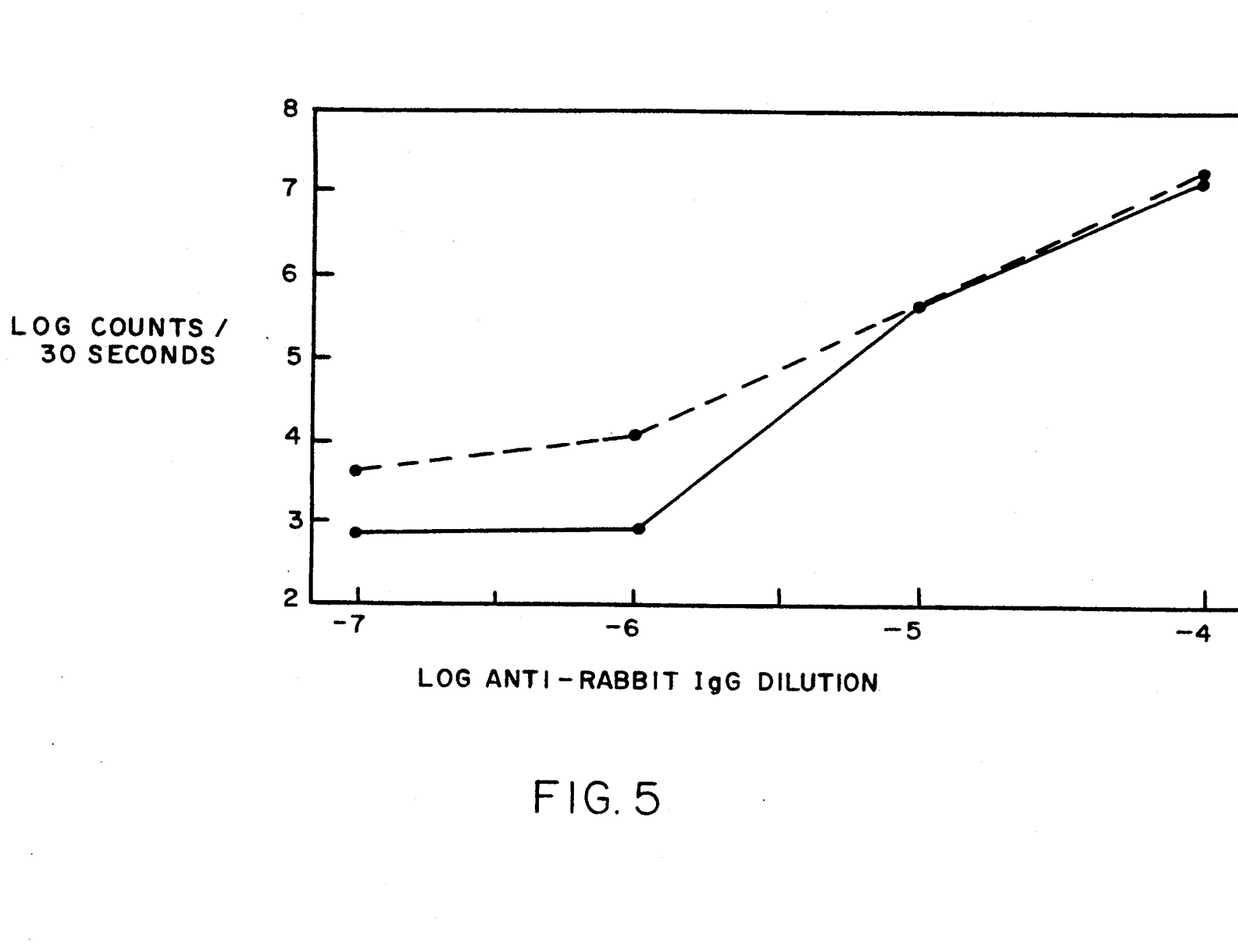
FIG. 5 is a graph showing the effect of UV light irradiation treatment on detection of antibody-IgG bound to solid phase. Log light produced is plotted on the y axis and log dilution of conjugate is plotted on the x axis. The line, —, represents results from not using the UV light treatment and, the line, ---, represents results after using UV light treatment.

More specifically, as is evident especially from the result of Example 5 and FIG. 5, since improvement of the assay linearity and the sensitivity can be attained according to the present invention, the present invention, particularly the technique of measurement of immunometrically bound enzyme to solid phase, can be applied to various competitive binding assays such as enzyme conjugated to an analyte and sandwich assays (enzyme antibody bend to an analyte which binds to solid phase antibody).

The following examples further illustrate the present invention in detail but are not to be construed to limit the scope thereof.

HRP used in examples 1 through 4 was that of Type VI purchased from Sigma Chemical Company, Saint Louis, Mo., U.S.A. This enzyme was dissolved in 0.1M Tris containing 0.01% BSA (pH 8.5). In experiments 1 through 4, the final dilution was that diluted 100 times with this buffer. p-Phenylphenol and luminol were purchased from Aldrich Chemical Company, Milwaukee, Wis., U.S.A. p-Phenyl-phenol was recrystallized from 43% ethanol. Luminol was used as it was without any purification. Luminol was also used after recrystallization 4 times from 5% NaOH [Stott and Kricka, Bioluminescence and Chemiluminescence, Second, 237-240, (1987)]. Methylene blue, rose bengal and eosin Y were purchased from Wako Pure Chemicals, Co., Ltd., Osaka, Japan and dissolved in 0.1M Tris (pH 8.5). Hydrogen peroxide was purchased from Wako Pure Chemicals, Co., Ltd. Ethanol used for dissolving p-phenylphenol was a high purity product manufactured by Wako Pure Chemicals, Co., Ltd. and all the enhancer containing solutions contained 1% of ethanol. All the other reagents were of analytical grade and all the solutions were prepared by distilled water. All the measurements were conducted at room temperature by using a tubular Chemilumino-meter (inner diameter: 12 mm, BLR 201 manufactured by Aloka Co., Ltd., Tokyo, Japan) and integrating experimental measurements for 10 seconds.

EXAMPLE 1

Irradiation of Luminol, Enhancer and HRP Solution with Ultraviolet Light

A 1.0 ml of 0.1M Tris solution (pH 8.5) containing p-phenylphenol (60 μM), luminol (200 μM) and HRP (0 or 125 atto-mol) in a glass test tube of 12 mm in diameter was irradiated with ultraviolet (UV) light of 200 to 400 nm (Toshiba PAN UV lamp PUV-1B, Tokyo Kogaku Kikai Co., Ltd., Tokyo, Japan) at a distance of 3 cm. After irradiation, 50 mM hydrogen peroxide (10 μl) was added. The contents of the tube were mixed briefly. The amount of luminescence from 50 to 60 seconds after addition of hydrogen peroxide was measured.

Figure 1:
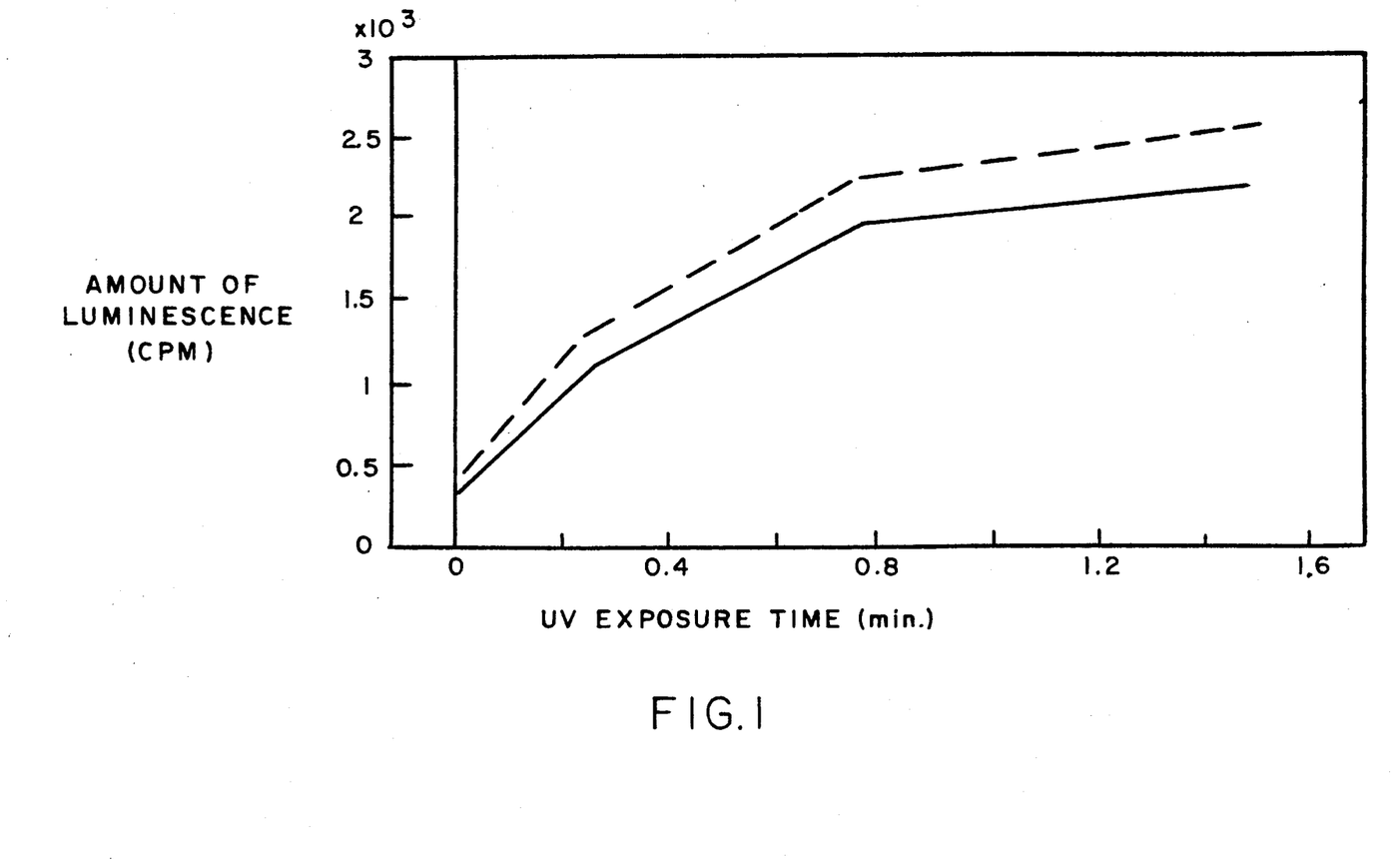
FIG. 1 is a graph showing the relationship between an amount of luminescence emitted from 50 to 60 seconds after addition of hydrogen peroxide following UV irradiation treatment and UV irradiation time. The line, ---, represents that 125 atto-mol of HRP is added and the line, —, represents that no HRP is added.

FIG. 1 shows the results obtained by irradiation of the solution of luminol and the enhancer with ultraviolet light. The luminescence count obtained by luminescence output in the presence of HRP at a concentration of 125 atto-mol/ml and that without HRP are increased with an increase in ultraviolet exposure time, respectively. However, the difference between the counts are clearly increased with the elapse of the ultraviolet exposure time and, after about 1 minute, the difference becomes almost constant. Replicates of two were used.

EXAMPLE 2

Irradiation of Luminol Solution with Ultraviolet Light

One ml of 0.1M Tris solution (pH 8.5) containing luminol (200 μM) in a glass test tube of 12 mm in diameter was irradiated with ultraviolet light of 200 to 400 nm (Toshiba lamp PUV-1B) at 3 cm range for 60 seconds. After irradiation, 50 mM hydrogen peroxide (10 μl), 60 μM p-phenylphenol and a HRP solution (10 μl) containing 0, 50, 100 or 200 pg of HRP were added. The contents of the tube were mixed briefly, and the amount of luminescence was measured at 10 to 20 seconds after addition of hydrogen peroxide. Sample replicates of 3 were used.

Figure 2:
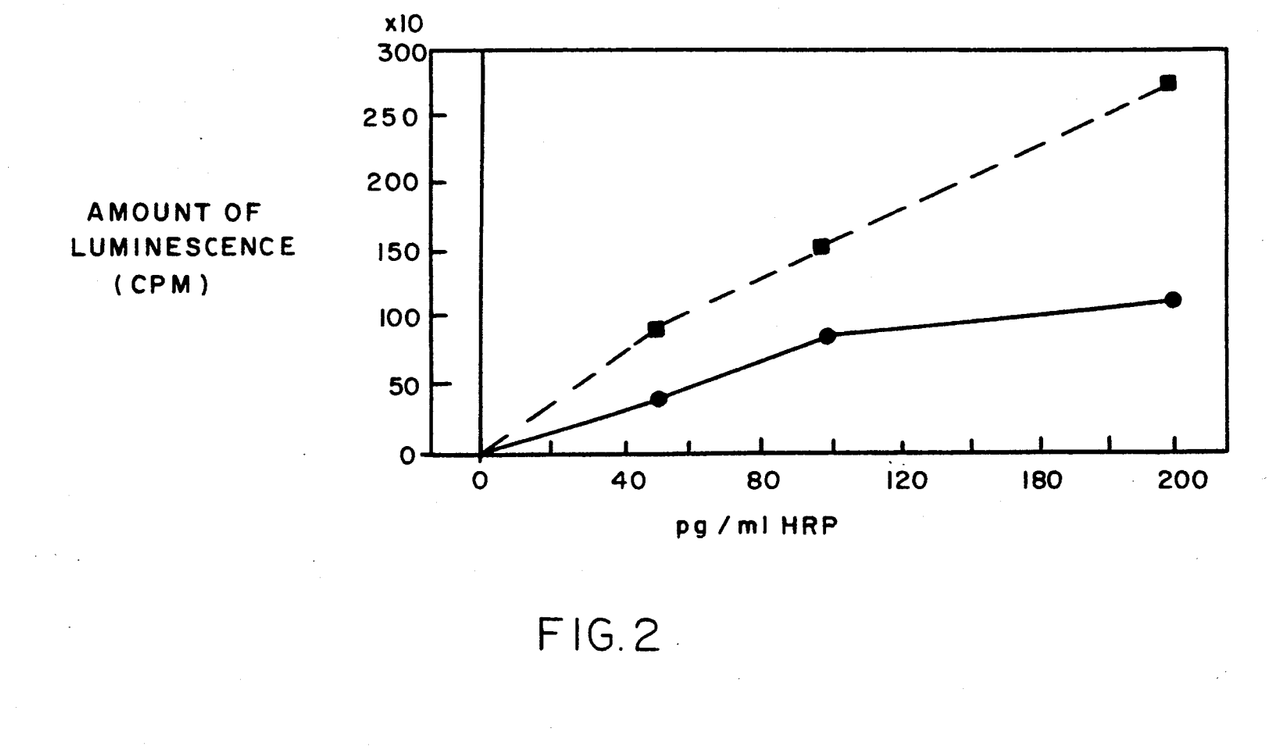
FIG. 2 is a graph showing the relationship between amount of HRP and amount of chemiluminescence. The line, ---●---, represents that no UV irradiation treatment is conducted; and the line, ---■---, represents that UV irradiation treatment is conducted.

The results are shown in FIG. 2. As seen from FIG. 2, a larger amount of luminescence is obtained in the case of conducting irradiation with ultraviolet (---■---) in comparison with that without irradiation (---●---).

As a result of a statistic analysis, the detection limit is 20 pg in the case of no irradiation with ultraviolet light and 5 pg in the case of irradiation with ultraviolet light. Namely, the sensitivity is increased 4 times by irradiation with ultraviolet light.

EXAMPLE 3

Formation of Free Radicals by Photosensitive Coloring Matter

One ml of 0.1M Tris solution containing EDTA (0.1 mM), luminol (4 mM) and a coloring matter in a concentration varying between 4 to 100 ng/ml was exposed to white light (20 W) at a distance of 4 cm for 1 minute. Then, 5 mM p-phenylphenol in ethanol (10 μl), 0 or 80 atto-mol HRP in 0.01% BSA-Tris buffer (10 μl) and 50 mM hydrogen peroxide (10 μl) solutions were added in turn and the contents mixed briefly. Luminescence was measured for 120 seconds.

When light irradiation was conducted for 60 seconds prior to addition of HRP, the luminescence output in the presence of a 80 atto-mol/ml HRP was improved by using methylene blue at a concentration of 16 ng/ml.

Figure 3:
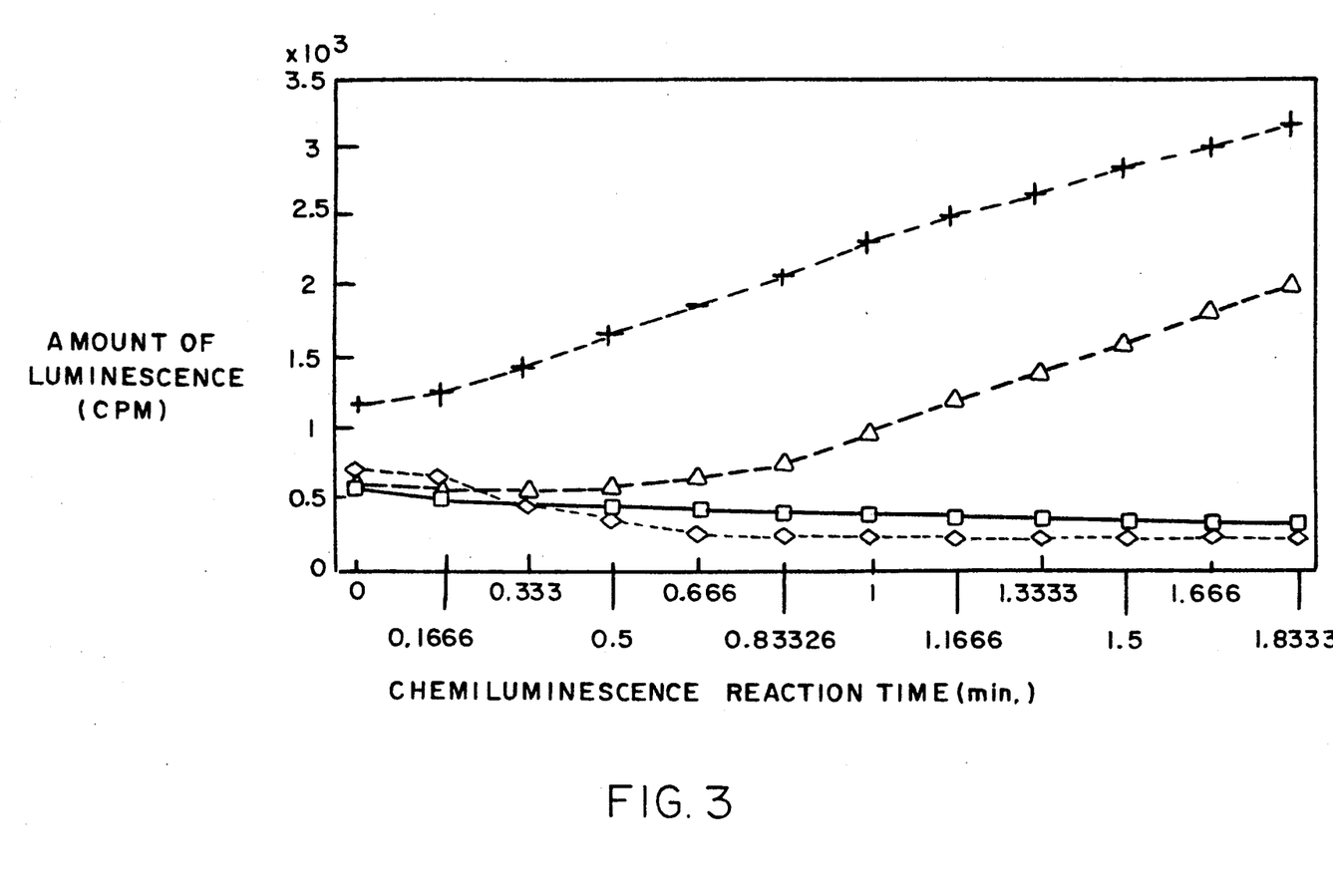
FIG. 3 is a graph showing the time-course of HRP reaction initiated by simultaneous addition of HRP and hydrogen peroxide 1 minute after white light irradiation treatment to show the effects of methylene blue treatment on the reaction. The line, ---◊---, represents that the dye and HRP are not used; the line, ---Δ---, represents that 80 atto-mol mol of HRP are used without addition of the dye; the line, ---□---, represents that 16 ng/ml of the dye are used without addition of HRP; and the line, ---+---, represents that 80 atto-mol of HRP and 16 ng/ml of the dye are used.

FIG. 3 shows the HRP reaction time-course initiated by addition of HRP and hydrogen peroxide after white light irradiation for 1 minute.

The conditions for using methylene blue in this example were optimized. Improvement by treatment with the coloring matter was maximum in the lowest HRP concentration range and the optimal concentration of the coloring matter was lowered as the HRP concentration decreased.

Although improvement in HRP catalyzed luminescence by the coloring matter was significant after 2 minutes reaction, it was most significant at the relatively shorter reaction time.

Figure 4:
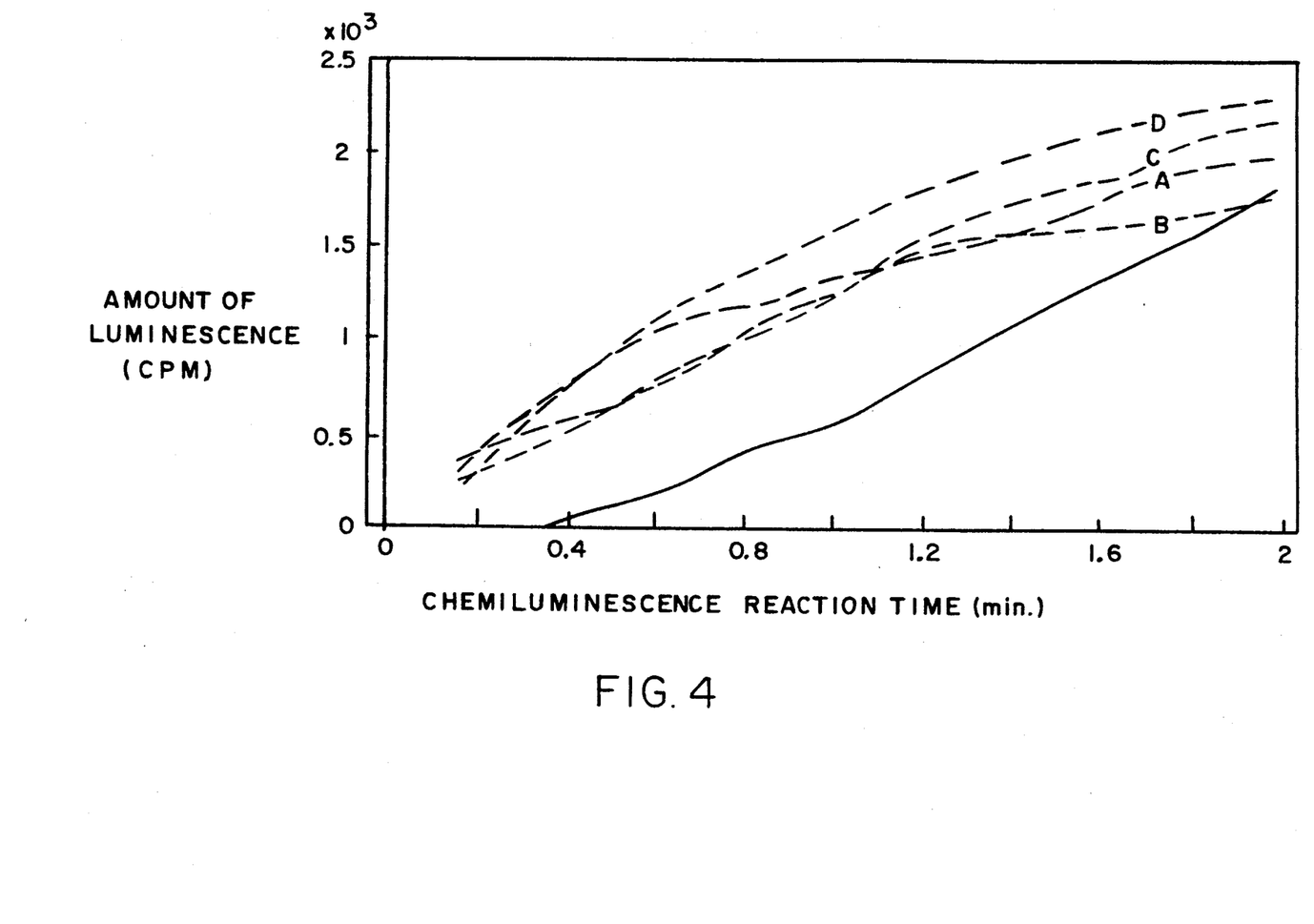
FIG. 4 is a graph showing the effects of various photosensitive substances on chemiluminescence under the action of 80 atto-mol of HRP (the background value being subtracted). The line, ---A---, represents eosin Y; the line, ---B---, represents resazurin; the line, ---C---, represents rose bengal; and the line, ---D---, represents flavin mononucleotide. The line, —, represents no addition of dye.

FIG. 4 shows luminescence output catalyzed by HRP in the presence of coloring matter at 0 to 2 minutes after addition of the enzyme. In this test, various photosensitive coloring matters are used at a concentration of 50 ng/ml. The concentration of the coloring matters were not optimized. It was found that all the coloring matters tested increased net luminescence output by the HRP catalyzing reaction following the irradiation treatment.

EXAMPLE 4

Use of Photosensitive Dyes and Recrystallized Luminol

A 1 ml of 0.1M Tris solution (pH 8.5) containing luminol (4 mM), p-phenylphenol (50 μM), EDTA (0.1 mM) and methylene blue (0 or 5 ng/ml) was prepared. After irradiation with white light according to the same manner as that described above, 0 or 25 atto-mol of HRP (10 μl) and 50 mM hydrogen peroxide (10 μl) were added to the solution and luminescence was measured for 120 seconds. This operation was repeated 4 times. The "limit of detection" was defined as the concentration of enzyme which generated an average photo-signal equivalent to the zero level enzyme signal plus three times the standard deviation of the background signal.

When using methylene blue, net luminescence was increased by 92% in the case of measurement at 50 to 60 seconds after addition of hydrogen peroxide, and by 52% in the case of measurement at 110 to 120 seconds after addition of hydrogen peroxide, respectively. When the measurement time took longer time than this, the photo signal began to decrease. The limit of detection was 9.3 atto-mol in the case of a sample without methylene blue, and 2.5 atto-mol in the case of a sample containing methylene blue at a concentration of 5 ng/ml. Thus, the limit of detection was improved 4 times by using methylene blue.

EXAMPLE 5

Improvement of Antibody Enzyme Conjugate Detection on Solid Phase by UV Treatment Polystyrene balls 4mm in diameter were coated by incubating rabbit serum (1 mg/ml protein) in pH 9.5 carbonate buffer for 80 min. These were washed in water three times and stored in dilution buffer (25% block ace (Snow Brand, Sapporo, Japan) 0.05M phosphate 0.6% NaCl pH 7) overnight. Goat anti-rabbit IgG labelled with HRP "IgG-HRP" (Miles-Yeda Inc Israel code 61-202) was diluted in dilution buffer 10,000 times, 100,000 times, 1,000,000 times and 10,000,000 times. Binding reactions were set up by separately incubating each ball in 100 μl of each IgG-HRP solution for 1 hr. The balls were rinsed three times with dilution buffer and stored in dilution buffer. Quantification of immunoadsorbed conjugate was carried out by the following method. One ml of 2mM luminol in tris buffer pH 8.7 was added to a tube of 12mm in diameter and the tube irradiated at a distance of 3 cm from a long wave 365 nm UV lamp (Series E Spectronics corp., Westbury, N.Y.) for one minute. Following this period a ball prepared by immunoreaction described above and 10 μl of 50mM hydrogen peroxide, 5mM phenylphenol were added and chemiluminescence from the tube measured for 30 seconds.

FIG. 5 shows the results of quantification of bound conjugate in this assay and compares the effect of UV treatment. These results show that measurement of low concentrations of antibody enzyme conjugate from immunometric assays can be improved by the UV treatment. In particular, the assay linearity and the sensitivity is improved.

What is claimed is:

1. An enzyme detection method comprising: carrying out an enzymatic reaction and a chemiluminescent reaction between enzymatic reaction components comprising a peroxidase enzyme, an oxidant and a chemilumigenic component; and detecting the produced chemiluminescence; and further comprising the step of irradiating the enzymatic reaction components with light having a wavelength spectrum within the range from the ultraviolet through the visible light spectrum, prior to carrying out the enzymatic reaction and the chemiluminescent reaction.

2. A method of claim 1, wherein the chemilumigenic component is luminol.

3. A method of claim 1, wherein the peroxidase enzyme is horseradish peroxidase.

4. A method of claim 1, wherein the light irradiation activates a photosensitive substance that forms free radicals upon photoactivation.

5. A method of claim 4, wherein the photosensitive substance is a member selected from the group consisting of methylene blue, fluorescein, eosin, erythrosine, rose bengal and flavin mononucleotide.

6. A method of claim 4, wherein the light has a spectrum which matches the absorption spectrum of the photosensitive substance used.

7. A method of claim 4, wherein the light has a wavelength corresponding to that of the maximum energy absorbance for the photosensitive substance used.

8. A method of claim 1 wherein ultraviolet light having a wavelength ranging from 200 to 400 nm is used.

* * * * *